(12) United States Patent
Schaller et al.

(10) Patent No.: US 11,751,909 B2
(45) Date of Patent: Sep. 12, 2023

(54) RETRACTABLE INSTRUMENT

(71) Applicant: Alcon Inc., Fribourg (CH)

(72) Inventors: Philipp Schaller, Stein Am Rhein (CH); Reto Grueebler, Greifensee (CH); Thomas Linsi, Schaffhausen (CH)

(73) Assignee: Alcon Inc., Fribourg (CH)

( * ) Notice: Subject to any disclaimer, the term of this patent is extended or adjusted under 35 U.S.C. 154(b) by 612 days.

(21) Appl. No.: 16/903,809

(22) Filed: Jun. 17, 2020

(65) Prior Publication Data

US 2020/0397476 A1     Dec. 24, 2020

Related U.S. Application Data

(60) Provisional application No. 62/865,343, filed on Jun. 24, 2019.

(51) Int. Cl.
| | | |
|---|---|---|
| *A61B 17/34* | (2006.01) | |
| *A61F 9/007* | (2006.01) | |
| *A61B 17/00* | (2006.01) | |

(52) U.S. Cl.
CPC ...... *A61B 17/3496* (2013.01); *A61B 17/3421* (2013.01); *A61B 17/3498* (2013.01);
(Continued)

(58) Field of Classification Search
CPC ............ A61B 17/3496; A61B 17/3421; A61B 17/3498; A61B 2017/3454;
(Continued)

(56) References Cited

U.S. PATENT DOCUMENTS 5,364,365 A * 11/1994 Wortrich ............ A61B 17/3496
604/164.12
9,192,515 B2    11/2015 Papac
(Continued)

FOREIGN PATENT DOCUMENTS

CN          202426711 U      9/2012

OTHER PUBLICATIONS

Alcon Global Vitreoretinal Product Catalog, 2014 (pp. 41-48).
(Continued)

*Primary Examiner* — Darwin P Erezo
*Assistant Examiner* — Brigid K Byrd
(74) *Attorney, Agent, or Firm* — PATTERSON & SHERIDAN, LLP

(57) ABSTRACT

A cannula assembly having a retractable cannula tip for use in ophthalmic surgical procedures is disclosed. The apparatus may include a housing having a valve bay disposed between its proximal and distal ends, and a cannula assembly, including an inner and outer tube, that extends from the distal end of the housing. The inner tube may include an elongated portion with a cannula tip at its distal end. The apparatus may further include a valve disposed in the valve bay of the housing. The valve may comprise a valve tubular for adjusting flow through the inner tube, and an actuator for moving the cannula tip from an extended position to a retracted position in the outer tube. The valve tubular may provide a biasing force to the inner tube in the retracted position to move the inner tube back to the extended position upon release of the actuator.

19 Claims, 8 Drawing Sheets

(52) U.S. Cl.
CPC .... *A61F 9/007* (2013.01); *A61B 2017/00199* (2013.01); *A61B 2017/00973* (2013.01); *A61B 2017/3454* (2013.01); *A61B 2217/005* (2013.01); *A61B 2217/007* (2013.01)

(58) Field of Classification Search
CPC ........... A61B 2017/00199; A61F 9/007; A61F 9/00–00781; A61F 9/013–0136
See application file for complete search history.

(56) References Cited

U.S. PATENT DOCUMENTS

| | | | |
|---|---|---|---|
| 9,730,834 B2 | 8/2017 | Charles | |
| 9,731,065 B2 | 8/2017 | Bourne | |
| 9,750,637 B2 | 9/2017 | Schaller | |
| 9,757,536 B2 | 9/2017 | Abt | |
| 9,878,075 B2 | 1/2018 | Sussman | |
| 2007/0260173 A1 | 11/2007 | Boukhny | |
| 2008/0167604 A1 | 7/2008 | Hong | |
| 2014/0171995 A1* | 6/2014 | McDonell | A61F 9/00736 606/170 |
| 2016/0008524 A1* | 1/2016 | Harder | A61M 1/84 604/158 |
| 2016/0067091 A1 | 3/2016 | Wells | |
| 2018/0296391 A1 | 10/2018 | Charles | |
| 2019/0374248 A1 | 12/2019 | Grueebler | |
| 2020/0179656 A1* | 6/2020 | Murakami | A61F 9/007 |
| 2020/0188561 A1 | 6/2020 | Grueebler | |
| 2020/0397477 A1 | 12/2020 | Schaller | |

OTHER PUBLICATIONS https://www.vitreq.com/uploads/brochures/Vitreq_BVI_Brochure_Backflush_2018.pdf (accessed May 29, 2020, appears to be dated Jun. 2018 (8 pages).
MedOne Backflush Cannulas brochure, dated 2018 (1 page).
MedOne Brochure, "Exactly What Your Looking For—High Quality Instruments for Vitreoretinal Surgery," 2012, 12pages.
DORC: Focus on Highlights catalog, 2012, pp. 9-11, 20, 34, 35.

* cited by examiner

RETRACTABLE INSTRUMENT

PRIORITY CLAIM

This application claims the benefit of priority of U.S. Provisional Patent Application Ser. No. 62/865,343 titled "Retractable Instrument", filed on Jun. 24, 2019, whose inventors are Philipp Schaller, Reto Grueebler, and Thomas Linsi, which is hereby incorporated by reference in its entirety as though fully and completely set forth herein.

TECHNICAL FIELD

The present disclosure generally relates to surgical instruments used in ophthalmic surgical procedures and, more particularly, to a cannula assembly having a cannula tip that is retractable.

BACKGROUND

Cannulas are one example of microsurgical instruments used in ophthalmic surgical procedures, such as retinal detachment surgery. By way of example, cannulas may be used to aspirate fluids such as blood, aqueous humor, and/or infusion fluids (e.g., balanced saline solutions). These cannulas are typically connected by tubing to the machine-induced vacuum source and the fluids are collected in a disposable cassette (e.g., at a control console). To prevent or avoid damage to the eye tissue in the event of contact with the eye, the cannula may have a tip formed from a soft, compliant material (e.g., silicone). This "soft" tip helps prevent damage to the delicate tissue of the eye in the event of physical contact with the eye, typically the retina.

During ophthalmic surgical procedures, the surgeon may require several different instruments throughout the procedure. This frequently requires that these instruments be repeatedly and/or sequentially inserted into and removed out of an incision that provides access to an interior portion of the eye. To guard against trauma to the incision from the repeated entry/exit of instruments, surgeons generally insert the instruments through an access cannula. The access cannula can also assist in maintaining the incision in an open position as well as enabling ready access to the incision. One type of access cannula comprises a narrow tube with an attached hub. The surgeon may make an incision on the eye (e.g., with a trocar through the sclera) and insert the tube of the access cannula through the incision up to the hub, which acts as a stop that prevents the tube from entering the eye completely. Valved cannulas were developed to address the issue of fluids flowing out of the tube when the tube is not connected to an infusion device or when an instrument is not inserted within the tube because the interior of the eye is pressurized.

In some instances, valved cannulas include a slit silicone diaphragm or cap on the outside of the hub. The slit provides an opening into the tube through which the surgical instrument can be inserted. However, a soft-tipped cannula may be insufficiently rigid to of open the slit without the application of undue pressure against the cannula. The soft tip may buckle or become stuck necessitating multiple trials before successful entry through the access cannula into the eye. If too much pressure is applied, the soft tip could even be sheared off, potentially falling into the eye during insertion and requiring remedial measures for removal of the soft tip from the eye.

SUMMARY

In an exemplary aspect, the present disclosure provides an apparatus for use in an ophthalmic surgical procedure. The apparatus may include a housing having a proximal end and a distal end with a valve bay disposed between the proximal end and the distal end. The apparatus may further include a cannula assembly that extends from the distal end of the housing, wherein the cannula assembly includes: an outer tube; and an inner tube positioned in the outer tube, wherein the inner tube includes an elongated portion and a cannula tip attached at a distal end of the elongated portion. The apparatus may further include a valve disposed in the valve bay of the housing, wherein the valve comprises a valve tubular coupled to the inner tube for adjusting flow through the inner tube; and an actuator coupled to the valve and the inner tube for moving the cannula tip from an extended position to a retracted position in the outer tube, wherein the valve tubular provides a biasing force to the inner tube in the retracted position to move the inner tube back to the extended position upon release of the actuator.

In another exemplary aspect, the present disclosure provides a system for ophthalmic surgical procedures. The system may include a console comprising a housing, a display screen supported by the console, and a processor. The system may further include a surgical instrument. The surgical instrument may include a housing having a proximal end and a distal end with a valve bay disposed between the proximal end and the distal end. The surgical instrument may further include a cannula assembly that extends from the distal end of the housing, wherein the cannula assembly includes: an outer tube; and an inner tube positioned in the outer tube, wherein the inner tube includes an elongated portion and a cannula tip attached at a distal end of the elongated portion. The surgical instrument may further include a valve disposed in the valve bay of the housing, wherein the valve comprises a valve tubular coupled to the inner tube for adjusting flow through the inner tube; and an actuator coupled to the valve and the inner tube for moving the cannula tip from an extended position to a retracted position in the outer tube, wherein the valve tubular provides a biasing force to the inner tube in the retracted position to move the inner tube back to the extended position upon release of the actuator. The system may further include a supply line configured to couple the surgical instrument to the console.

In yet another exemplary aspect, the present disclosure provides a method for operating a surgical instrument. The method may include providing the surgical instrument that includes a housing, a cannula assembly that extends from a distal end of the housing, and a valve tubular disposed in a valve bay of the housing. The cannula assembly may include an outer tube and an inner tube disposed in the outer tube, wherein the valve tubular is operable for adjusting flow through the inner tube of the cannula assembly. The method may further include retracting a cannula tip of the inner tube into the outer tube, wherein the retracting causes the valve tubular to deform and generate spring energy. The method may further include inserting the cannula assembly through a working cannula and into an eye while the cannula tip is retracted into the outer tube.

It is to be understood that both the foregoing general description and the following drawings and detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following.

BRIEF DESCRIPTION OF THE DRAWINGS

These drawings illustrate examples of certain aspects of some of the embodiments of the present disclosure and should not be used to limit or define the disclosure.

DETAILED DESCRIPTION

Figure 1:
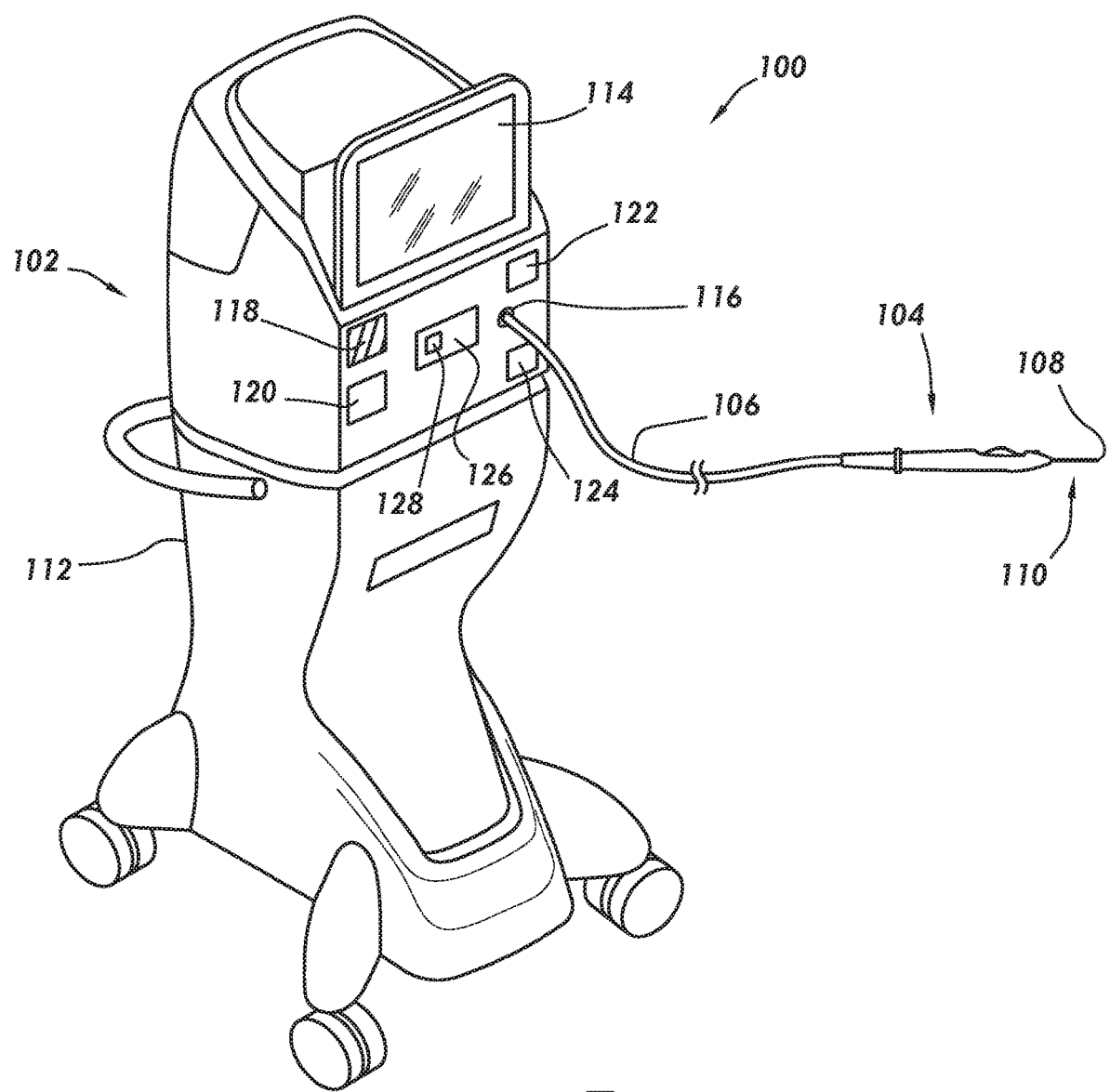
FIG. 1 illustrates an example surgical system according to particular embodiments of the present disclosure.

For the purposes of promoting an understanding of the principles of the present disclosure, reference will now be made to the implementations illustrated in the drawings and specific language will be used to describe them. It will nevertheless be understood that no limitation of the scope of the disclosure is intended. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with reference to one or more implementations may be combined with the features, components, and/or steps described with reference to other implementations of the present disclosure. For simplicity, in some instances the same reference numbers are used throughout the drawings to refer to the same or like parts.

The present disclosure generally relates to surgical instruments used in ophthalmic surgical procedures and, more particularly, to a cannula assembly having a cannula tip that is retractable. Certain cannula tips, such as soft tips, may be difficult to insert into the eye through the working cannula. In accordance with example embodiments disclosed herein, the cannula assembly may be provided with a cannula tip that is retractable. During insertion in the eye, the cannula tip may be retracted, for example, to facilitate insertion through the working cannula. After insertion into the eye, the cannula tip may be extended prior to use. Therefore, the apparatus, systems, and methods of the present embodiments may allow for insertion of the soft-tipped cannula assemblies through the working cannula and into the eye without buckling or potential damage to the soft tip.

FIG. 1 illustrates a surgical system 100 according to a particular embodiment of the present disclosure. As illustrated, the surgical system 100 may include a console 102, a surgical instrument 104, and a supply line 106 coupling the surgical instrument 104 to the console 102. In the illustrated embodiment, the surgical instrument 104 comprises a cannula assembly 110 having a cannula tip 108 that is retractable. One embodiment of the surgical instrument 104 will be described in more detail below with respect to FIG. 2. It should be understood that the surgical system 100 shown in FIG. 1 is merely an example, and the surgical instrument 104 may be used with alternatively configured systems.

In some embodiments, the console 102 may comprise a housing 112 and an associated display screen 114. As illustrated, the housing 112 may be a mobile base that supports the display screen 114 and other components of the console 102. The display screen 114 may show data relating to system operation and performance during a surgical procedure. During ophthalmic surgery, the surgical instrument 104 may be coupled to the console 102 by the supply line 106. By way of example, the supply line 106 may comprise a flexible plastic, silicone, or rubber tubing and/or electric cabling. In some embodiments, the supply line 106 may be fluidically coupled with a surgical cassette (not shown) to operatively connect to the surgical instrument 104 through one or more ports 116 in the housing 112. In some embodiments, the supply line 106 comprises aspiration lines, power lines, and/or irrigation lines. In some embodiments, the supply line 106 may facilitate control and monitoring the surgical instrument 104 by also transmitting data between the surgical instrument 104 and the console 102. In other embodiments, data may be transferred wirelessly between the surgical instrument 104 and the console 102.

In some embodiments, the console 102 further may comprise one or more processors 118 in communication with a memory 120. The processor 118 may include computer-instructions to control the surgical instrument 104, display information on the display screen 114, and/or receive and process input commands and data. In some embodiments, the surgical system 100 may include a data transmission module 122. In some embodiments, the surgical system 100 may include a network interface 124 for communication with a network. In the illustrated embodiment, the surgical system 100 includes a user interface 126 that enables the user to input data and/or command signals.

For example, in one embodiment, the user interface 126 may include a control element 128 that allows the user to trigger a state change in the surgical instrument 104. In some embodiments, the control element 128 comprises a button that may be depressed to activate the state change. In other embodiments, the control element 128 comprises a plurality of buttons with each button configured to activate and/or deactivate different functions of the surgical instrument 104. However, the control element 128 may comprise any of a variety of ON/OFF switches, buttons, toggles, wheels, footswitches, or other user input devices. In some embodiments, the control element 128 may be additionally or alternatively disposed on the surgical instrument 104. These features may facilitate control of the surgical instrument 104 during operation.

The processor 118 may be any suitable processor, including, but not limited to, an integrated circuit with power, input, and output pins capable of performing logic functions.

For example, the processor 118 may perform logic functions based on inputs from the control element 128 to affect the state change of the surgical instrument 104. In some embodiments, the processor 118 controls the supply of power from a power source (not shown) to the surgical instrument 104 and/or signal commands to the surgical instrument 104. In various embodiments, the processor 118 may be a targeted device controller or a microprocessor configured to control more than one component of the surgical instrument 104 or a combination thereof. The processor 118 may include one or more programmable processor units running programmable code instructions for controlling the surgical instrument 104, among other functions. For example, in some embodiments, the processor 118 can control the aspiration and/or backflush functions of the surgical instrument 104.

The processor 118 may be wirelessly coupled to a computer (not shown) and/or other types of processor-based devices suitable for a variety of ocular applications. In various embodiments, the processor 118 can receive input data from a user, the control element 128, the surgical instrument 104, and/or various accessory devices via wireless or wired mechanisms. The processor 118 may use such input data to generate control signals to control or direct the operation of the surgical instrument 104. In some embodiments, the processor 118 is in direct wireless communication with the surgical instrument 104 and can receive data from and send commands to the surgical instrument 104.

The memory 120 may any suitable memory, including, but not limited to, semiconductor memory, such as Random-Access Memory (RAM), Ferroelectric RAM (FRAM), or flash memory, for interfacing with the processor 118. As such, the processor 118 can write to and read from the memory 120, and perform other common functions associated with managing semiconductor memory. For example, a series of tissue characterizations and/or command sequences can be stored in the memory 120.

Figure 2:
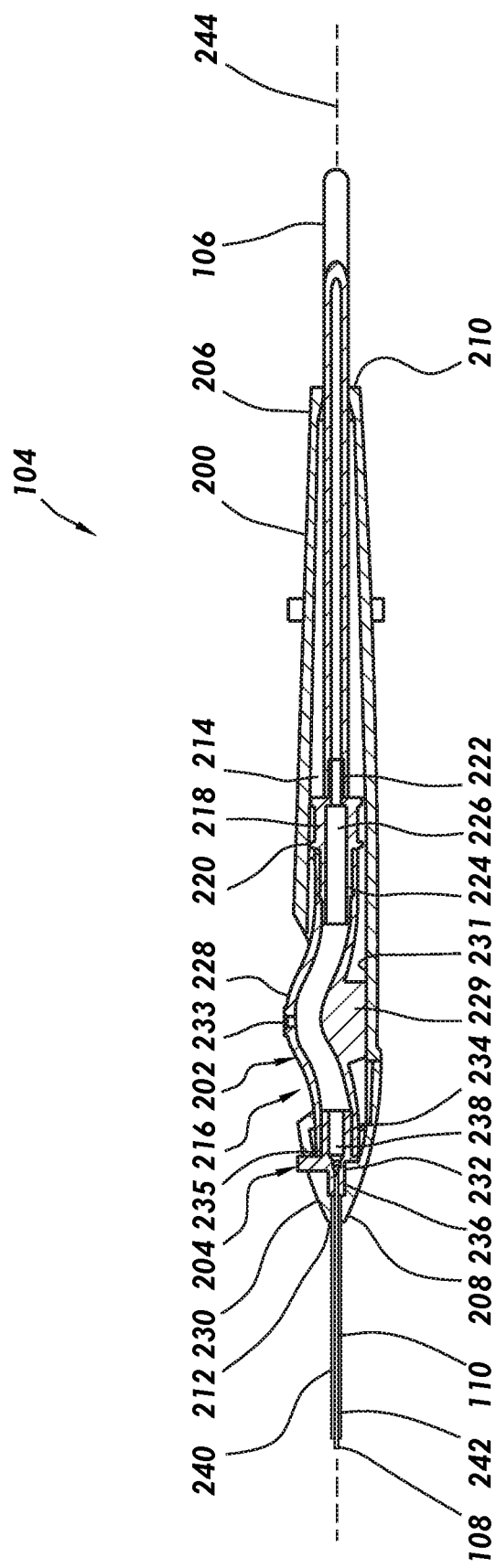
FIG. 2 is a cross-sectional side view of an example surgical instrument according to particular embodiments of the present disclosure.

FIG. 2 illustrates a cross-sectional side view of the surgical instrument 104 according to particular embodiments of the present disclosure. As illustrated, the surgical instrument 104 may include a housing 200, a valve 202 disposed in the housing 200, an actuator 204 coupled to the valve 202, and a cannula assembly 110 extending from the housing 200 and having a cannula tip 108. The actuator 204 may be operable to retract the cannula tip 108 upon actuation. In some embodiments, the valve 202 may provide a biasing force such that the cannula returns to an extended position upon release of the actuator 204.

The housing 200 may include a proximal end 206 and a distal end 208. A proximal port 210 may be formed in the housing 200 at the proximal end 206 for receiving the supply line 106. A distal port 212 may be formed in the housing 200 at the distal end 208 for receiving the cannula assembly 110. Housing 200 may define an interior chamber 214 that extends from proximal end 206 to a valve bay 216. In some embodiments, the housing 200 may be a single unitary piece. In alternative embodiments, the housing 200 may include more than one cylindrical piece. Moreover, the housing 200 may be constructed in any desirable manner from any number of components.

In some embodiments, a valve connection mechanism 218 may be disposed in the interior chamber 214 between the valve bay 216 and the proximal end 206. The valve connection mechanism 218 may couple the valve 202 to the supply line 106. The valve connection mechanism 218 may be any suitable device for fluidically connecting the valve 202 and the supply line 106. For example, the valve connection mechanism 218 may include a body 220 having a proximal extension 222 and a distal extension 224. The valve connection mechanism 218 may define a lumen 226 extending through the valve connection mechanism 218 for fluidically coupling the supply line 106 and the valve 202. In the illustrated embodiment, the supply line 106 may be coupled to the proximal extension 222 from the valve connection mechanism 218 and the valve tubular 228 (discussed in more detail below) may be coupled to the distal extension 224 from the valve connection mechanism 218. Any suitable technique may be used for securing the valve tubular 228 and the supply line 106 to the valve connection mechanism 218, including, but not limited to, a press fitting, adhesives, insert molding, and/or fasteners.

The valve 202 may be positioned in the valve bay 216 formed in the housing 200. In some embodiments, the valve 202 may include a valve tubular 228, for example, that extends from valve bay 216 into the interior chamber 214 of the housing 200. In the interior chamber 214, the valve tubular 228 may be coupled to the valve connection mechanism 218. The valve tubular 228 may also extend into housing nose 230 at distal end 208 of the housing 200. The valve tubular 228 may include a base 229 that secures the valve tubular 228 to an interior wall 231 of the valve bay 216. In the illustrated embodiment, a hole 233 may be formed in valve tubular 228. During surgery, a suction may be applied to the valve 202 by the console 102 through the supply line 106. When the hole 233 is unobstructed, the suction should typically bypass the cannula assembly 110. However, when the hole 233 is closed, the suction should be applied to the cannula assembly 110 for drawing fluid and/or materials from the eye through the cannula assembly 110. Any suitable technique may be used for closing the hole 233, including, but not limited to, an operator obstructing the hole 233 with a finger, thus, closing the valve 202.

In some embodiments, the valve tubular 228 may adapted to provide a biasing force to the cannula tip 108. For example, the valve tubular 228 may be made from a material that is flexible and elastic so that the valve tubular 228 may flex when force is applied by the actuator 204 but return to its original position when the force is removed. When flexed or otherwise deformed, the valve tubular 228 may store spring energy in the form of a biasing force to return to its original position when the force is removed. The valve tubular 228 may be formed from materials including, for example, silicone, polyurethane, polyethylene, polypropylene, polystyrene, polytetrafluoroethylene, fluorinated ethylene propylene (FEP), perfluoroalkoxy (PFA), polyether ether ketone (PEEK), polyetherimide (PEI), polyamide imide (PAI), thermoplastic polyimides (TPI), rubber, combinations thereof, or other medically compatible polymers or plastic compounds. However, the disclosure is not limited to use of these particular materials and one of ordinary skill in the art, with the benefit of this disclosure, should be able to select a material for use in the valve tubular 228.

In some embodiments, a cannula connection mechanism 232 may be disposed in the housing nose 230. The cannula connection mechanism 232 may connect the valve 202 to the cannula assembly 110. Cannula connection mechanism 232 may be any suitable device for fluidically connecting the valve 202 and the cannula assembly 110. For example, the cannula connection mechanism 232 may include a body 235 having a proximal extension 234 and a distal extension 236. The cannula connection mechanism 232 may define a lumen 238 extending through the cannula connection mechanism 232 for fluidically coupling the supply line 106 and the valve 202. In the illustrated embodiment, the valve tubular 228 may be coupled to the proximal extension 234, and the inner tube 240 of the cannula assembly 110 may be coupled to the distal extension 236. Any suitable technique may be used for securing the valve 202 and the cannula assembly 110 to the cannula connection mechanism 232, including, but not limited to, a press fit, adhesives, insert molding, and/or fasteners.

The actuator 204 may be coupled to the valve 202. In the illustrated embodiment, the actuator 204 is coupled to the valve 202 by way of the cannula connection mechanism 232. In alternative embodiments, the actuator 204 may be directly coupled to the valve 202. For example, the actuator 204 may be an exterior surface of the valve tubular 228. As illustrated, the actuator 204 may extend from the cannula connection mechanism 232 through the housing nose 230. In the illustrated embodiment, the actuator 204 may be a protrusion that extends from the cannula connection mechanism 232. The actuator 204 may be coupled to the cannula connection mechanism 232 by any suitable technique, including, but not limited to, adhesives, insert molding, and fasteners. In some embodiments, the actuator 204 and the cannula connection mechanism 232 may be unitary. In other embodiments, the actuator 204 and the cannula connection mechanism 232 may be separate components. To retract the cannula tip 108, the actuator 204 may be actuated to move the cannula tip 108 longitudinally toward proximal end 206 with respect to outer tube 242. Actuator 204 may be slidably disposed in a slot (not illustrated) or other opening formed in the housing nose 230.

Figure 3:
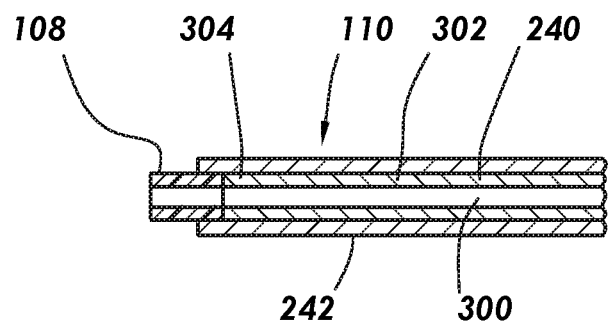
FIG. 3 is an exploded view of the cannula assembly show on FIG. 2.

With additional reference to FIG. 3, embodiments of the cannula assembly 110 may include an inner tube 240 and an outer tube 242. As illustrated, the inner tube 240 may be disposed in the outer tube 242. In some embodiments, the inner tube 240 may be slidably disposed in the outer tube 242, for example, such that the cannula tip 108 can be retracted into the outer tube 242, in accordance with present embodiments. As best seen on FIG. 2, cannula assembly 110 may be coupled to housing 200. For example, cannula assembly 110 may be coupled to the housing nose 230. As illustrated, cannula assembly 110 may extend from distal end 208 of the housing 200 with a portion of the cannula assembly 110 extending into the housing 200 through the distal port 212. For example, the cannula assembly 110 may extend into the housing nose 230 through the distal port 212.

Outer tube 242 may be coupled to the housing 200, for example, to the housing nose 230. Any suitable technique may be used for securing the outer tube 242 to the housing 200, including, but not limited to, press fitting, adhesives, insert molding, and fasteners. In some embodiments, the outer tube 242 may be attached to the cannula connection mechanism 232. The outer tube 242 may be formed from any suitable material. For example, suitable materials for the outer tube 242 may include, for example, a metal, such as stainless steel or titanium. However, the outer tube 242 may be formed from any suitable material, including, but not limited to, a polymer, metal, ceramic, or other suitable material.

Inner tube 240 may be coupled to the housing 200. For example, the inner tube 240 may be coupled to the cannula connection mechanism 232. In some embodiments, the inner tube 240 may be secured to the cannula connection mechanism 232 while the outer tube 242 may be secured to the housing 200, allowing for translation of the inner tube 240 with respect to the outer tube 242. Any suitable technique may be used for securing the inner tube 240 to the cannula connection mechanism 232, including, but not limited to, press fitting, adhesives, insert molding, and fasteners. As best seen on FIG. 3, the inner tube 240 defines lumen 300 and may include an elongated portion 302 and cannula tip 108, as best seen on FIG. 3. The elongated portion 302 may be formed from any suitable material. For example, suitable materials for the elongated portion 302 may include, for example, a metal, such as stainless steel or titanium. However, the elongated portion 302 may be formed from any suitable material, including, but not limited to, a polymer, metal, ceramic, or other suitable material.

With continued reference to FIG. 3, the cannula tip 108 may be coupled at a distal end 304 of the elongated portion 302. Any suitable technique may be used for coupling the cannula tip 108 and the elongated portion 302. For example, coupling the cannula tip 108 and the elongated portion 302 may be accomplished with extrusion, casting, molding, injection molding, insert molding, welding, adhesives, or other desired or suitable methods. In some embodiments, the coupling may be accomplished using a combination of two or more of these methods. The elongated portion 302 may have any suitable dimensions. For example, the elongated portion 302 may have a length of about 25 millimeters to about 45 millimeters. By way of further example, the elongated portion 302 may have an inner diameter of about 0.3 millimeters to about 0.4 millimeters. In some embodiments, the elongated portion may have a gauge size from 23 gauge to 27 gauge. The cannula tip 108 may also have any suitable dimensions. For example, the cannula tip 108 may have a length of about 0.5 millimeters to about 5 millimeters. By way of further example, the cannula tip 108 may have an inner diameter of about 0.1 millimeters to about 0.5 millimeters. Further, an exterior size and shape of the cannula tip 108 may correspond to the size and shape of the elongated portion 302, thereby producing a smooth transition between the elongated portion 302 and the cannula tip 108. In some embodiments, the cannula tip 108 and the elongated portion 302 may be unitary with the cannula tip 108 being an extension of the elongated portion 302.

In some embodiments, the cannula tip 108 may be adapted to provide a cushioning and/or non-abrasive engagement with delicate tissues or membranes, such as in a patient's eye. In some instances, the cannula tip 108 may be formed from any suitable, soft material. Particularly, in some instances, the cannula tip 108 may be formed from any medically compatible soft material. The cannula tip 108 may be formed from materials including, for example, silicone, polyurethane, polyethylene, polypropylene, polystyrene, polytetrafluoroethylene, fluorinated ethylene propylene (FEP), perfluoroalkoxy (PFA), polyether ether ketone (PEEK), polyetherimide (PEI), polyamide imide (PAI), thermoplastic polyimides (TPI), rubber, combinations thereof, or other medically compatible polymers or plastic compounds. In some embodiments, the material forming the cannula tip 108 may have a durometer value of 80 A. In other instances, the material forming the cannula tip 108 may have a durometer value of about 40 A to 50 D. As used herein, durometer values are Shore hardness values as measured using ASTM D2250 type A and type D scales. However, this disclosure is not so limiting. Rather, these hardness values are provided merely as examples. Thus, the material forming the cannula tip 108 may have any desired hardness. In some embodiments, the elongated portion 302 and cannula tip 108 may comprise the same or similar materials.

In operation, the actuator 204 may be used for retraction of the cannula tip 108. An operator may move actuator 204 along longitudinal axis 244 toward proximal end 206 to, in turn, also move cannula connection mechanism 232 and inner tube 240 along longitudinal axis such that cannula tip 108 retracts into outer tube 242. In response to movement of the actuator 204 along the longitudinal axis, embodiments may include deformation of the valve tubular 228, thereby storing spring energy. When the actuator 204 is released or applied pressure on the actuator 204 is reduced, the valve tubular 228 should return to its initial position moving the inner tube 240 and the cannula tip 108 distally such that the cannula tip 108 extends from the outer tube 242.

Figure 4A:
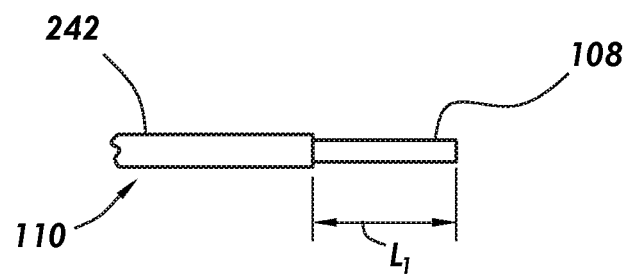
FIGS. 4a to 4c are side views showing different positions of a cannula tip according to particular embodiments of the present disclosure.
Figure 4B:
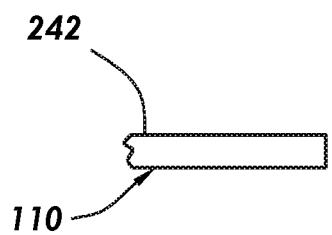
Figure 4C:
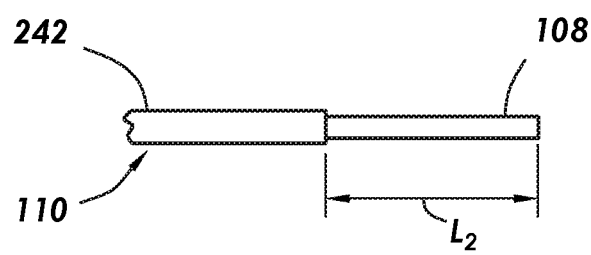

Turning now to 4A-4C, different positions of the cannula tip 108 are illustrated in accordance with embodiments of the present disclosure. FIG. 4A illustrates the cannula tip 108 in an initial (or extended) position. As illustrated, the cannula tip 108 may extend a distance of $L_1$ beyond the outer tube 242. The cannula tip 108 may extend any suitable distance $L_1$ beyond the outer tube 242, for example, a distance $L_1$ of about 0.5 millimeters to about 8 millimeters. FIG. 4B illustrates the cannula tip 108 retracted into the outer tube 242. The cannula tip 108 is not shown on FIG. 4B as the cannula tip 108 is fully retracted into the outer tube 242. FIG. 4C illustrates the cannula tip 108 in a second extended position. In the second extended position, the cannula tip 108 may extend a distance $L_2$ beyond the outer tube 242 that is larger than the distance $L_1$. In some embodiments, the actuator 204 can move forward to the distal end 208 of the housing 200 beyond its initial position to further extend the cannula tip 108 beyond its initial position. In the second extended position, the cannula tip 108 may extend any suitable distance $L_2$ beyond the outer tube 242, for example, a distance $L_1$ of about 0.7 millimeters to about 10 millimeters.

Figure 5:
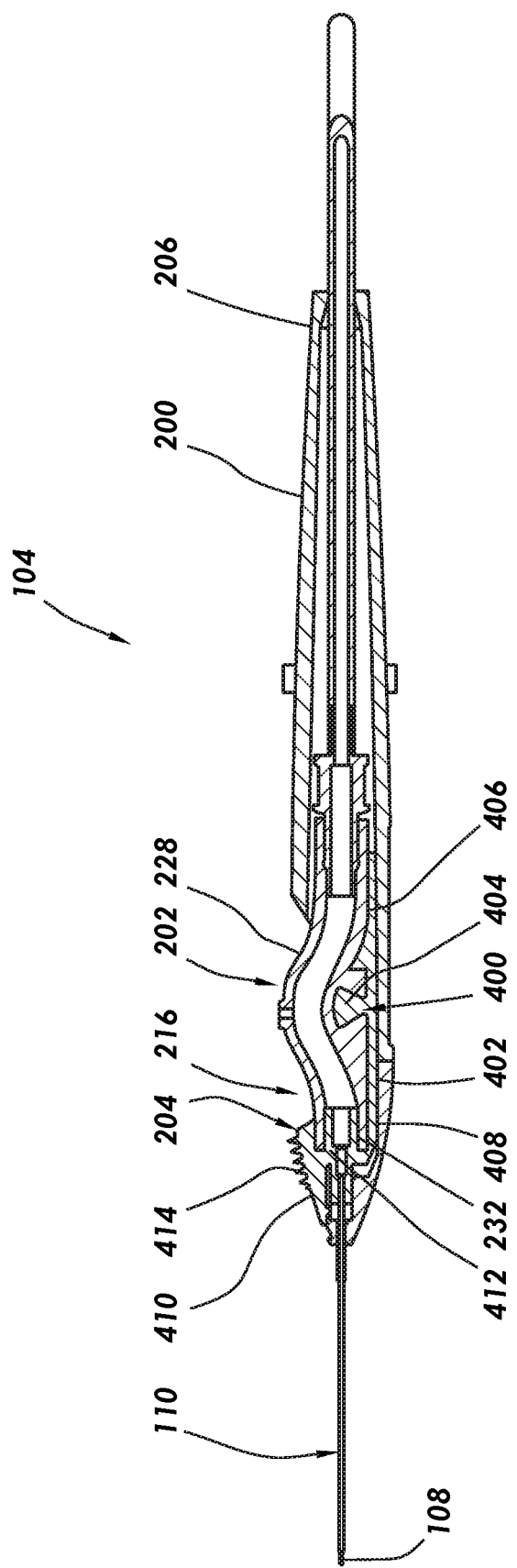
FIG. 5 is a cross-sectional side view of another example surgical instrument according to particular embodiments of the present disclosure.

FIG. 5 illustrates a cross-sectional side view of another embodiment of the surgical instrument 104 according to embodiments of the present disclosure. As illustrated, the surgical instrument 104 may include a housing 200, a valve 202 disposed in the housing 200, an actuator 204 coupled to the valve 202, and a cannula assembly 110 extending from the housing 200 and having a cannula tip 108. The actuator 204 may be operable to retract the cannula tip 108 upon actuation. In some embodiments, the valve 202 may provide a biasing force such that the cannula returns to an extended position upon release of the actuator 204.

In the illustrated embodiment, the surgical instrument 104 includes a sled 400. The sled 400 may be disposed in the valve bay 216 of the housing 200. In some embodiments, the sled 400 may be slidably disposed in the valve bay 216 such that upon application of backwards force on the actuator 204, the sled 400, and in turn the valve 202, may translate rearward toward proximal end 206. As illustrated, the sled 400 may include base 402 having a protrusion 404 that supports valve tubular 228. The base 402 may also have a rear-facing ramp 406 positioned proximally to the protrusion 404. At a distal end 408, the sled 400 may include the cannula connection mechanism 232 that may be integrally formed with, or otherwise connected to, the base 402. As previously described, the cannula connection mechanism 232 may couple the valve 202 to the cannula assembly 110. The actuator 204 may be include a slider button 410 coupled to the cannula connection mechanism 232 by connector piece 412. Slider button 410 may further include ridges 414 for providing a textured surface for facilitating gripping by a finger. However, it should be understood that other configurations of the actuator 204 are contemplated. For example, the slider button 410 may be made without the ridges 414.

Figure 6A:
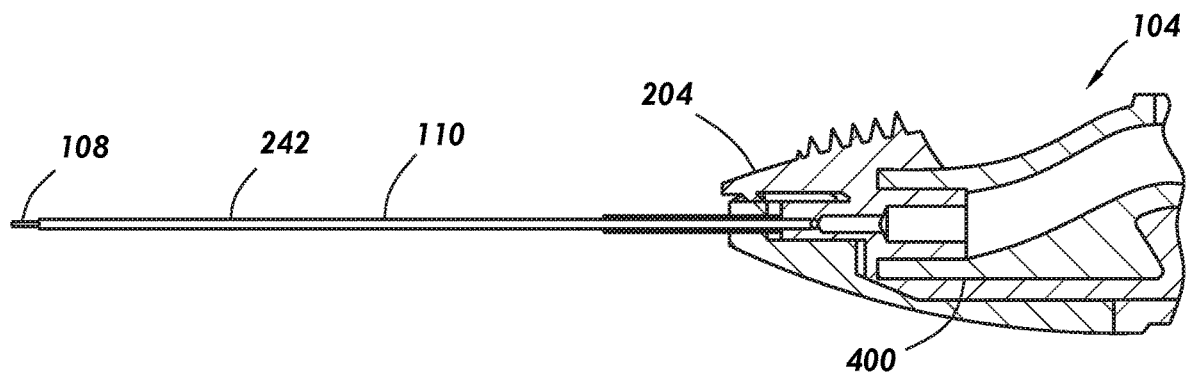
FIGS. 6a and 6b are close-up views of the example surgical instrument of FIG. 5 in different positions.
Figure 6B:
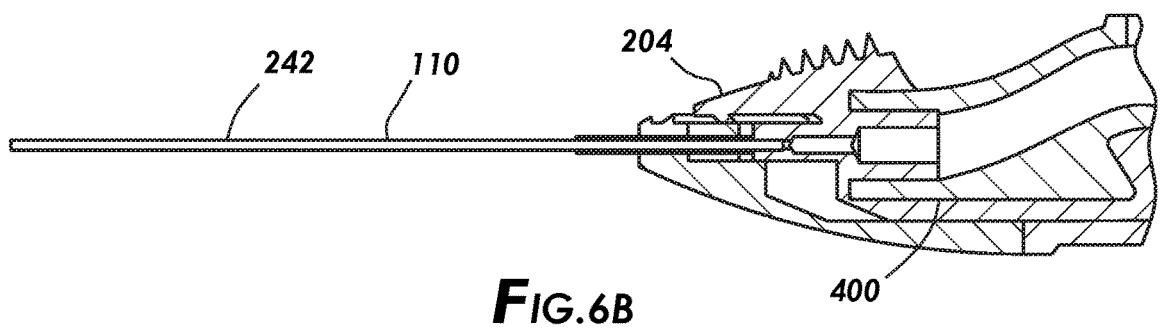

FIGS. 6a and 6b illustrate retraction of the cannula tip 108 in accordance with embodiments of the present disclosure. FIG. 6a illustrates the cannula tip 108 in an initial (or extended) position. In some embodiments, the actuator 204 may be used for retraction of the cannula tip 108. An operator may move actuator 204 backward to, in turn, also move sled 400 and inner tip backward such that cannula tip 108 retracts into outer tube 242. FIG. 6B illustrates the cannula assembly 110 in a retracted position with the cannula tip 108 being obstructed from view and fully retracted into the outer tube 242.

Figure 7:
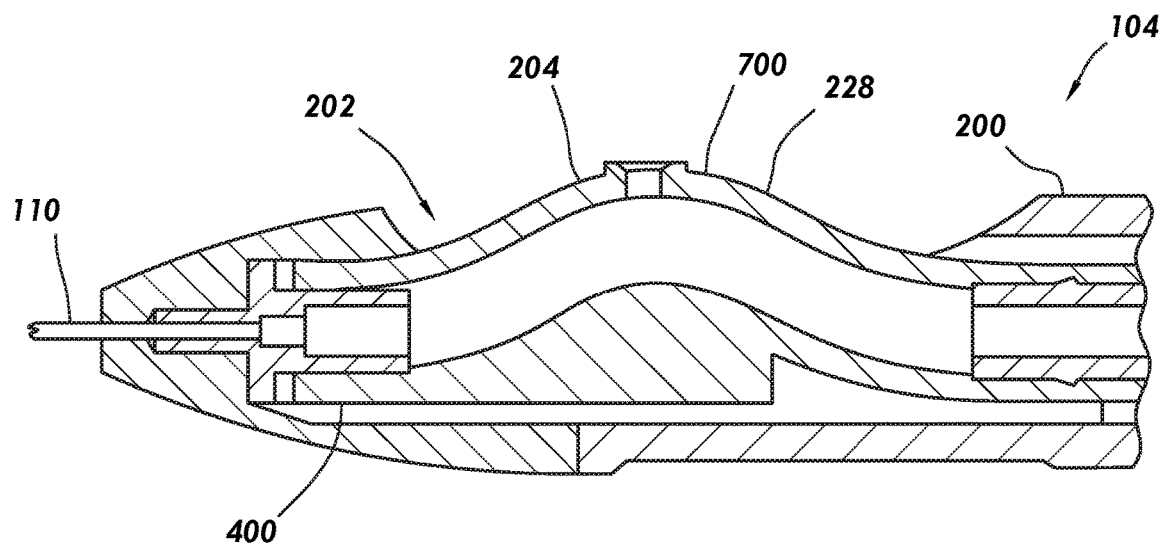
FIG. 7 is a cross-sectional side view of yet another example surgical instrument according to particular embodiments of the present disclosure.

FIG. 7 illustrates a cross-sectional side view of another embodiment of the surgical instrument 104 according to embodiments of the present disclosure. As illustrated, the surgical instrument 104 may include a housing 200, a valve 202 disposed in the housing 200, an actuator 204 coupled to the valve 202, and a cannula assembly 110 extending from the housing 200. In contrast to previous embodiments, the actuator 204 of FIG. 7 is an exterior surface 700 of the valve tubular 228. For actuation, rearward force may be applied to the exterior surface 700 to slide the actuator 204 rearward, which in turn moves the sled 400 rearward.

Figure 8:
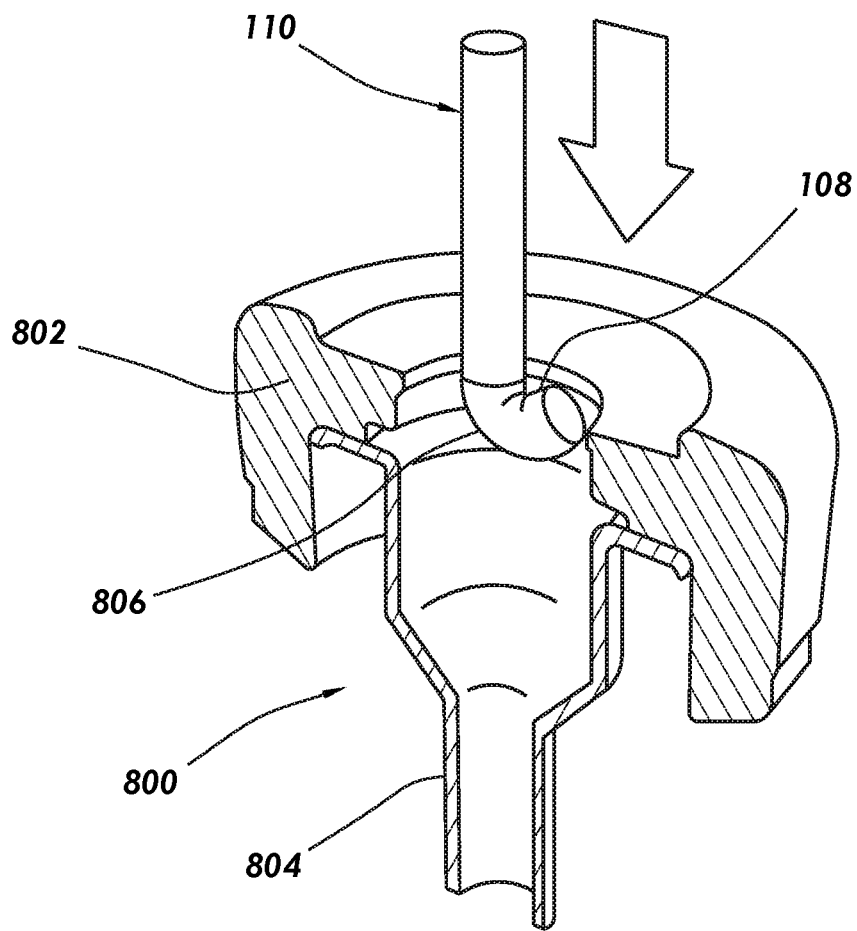
FIG. 8 is a partial cross-sectional view showing an exemplary cannula being inserted through an access cannula.

FIG. 8 illustrates an example of a working cannula 800 in accordance with embodiments of the present disclosure. The working cannula 800 may include a hub 802 connected to a hollow tube 804. The hub 802 of the working cannula 800 may include a valve 806, which may be in the form of a slitted silicone diaphragm. In operation, a cannula assembly 110 may be inserted through the valve 806. However, if the cannula tip 108 is not retracted prior to insertion, the cannula tip 108 may undesirably bend rather than passing through the valve 806, as illustrated in FIG. 8. Accordingly, particular embodiments of the present disclosure disclose retraction of the cannula tip 108 to facilitate insertion through the working cannula 800.

Figure 9:
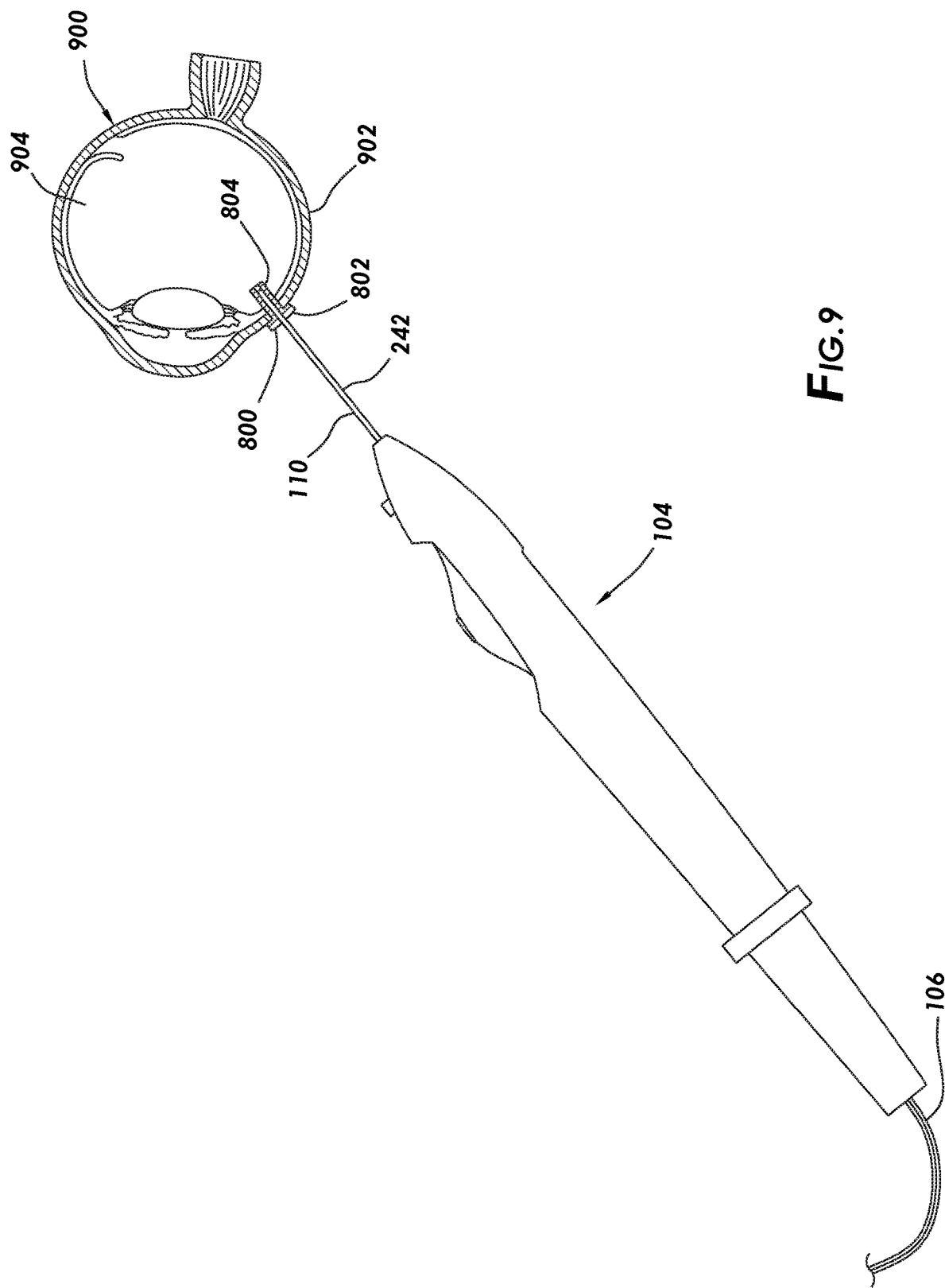
FIG. 9 is a partial cross-sectional view showing an exemplary surgical instrument being inserted through an access cannula with the cannula tip in a retracted position according to particular embodiments of the present disclosure.
Figure 10:
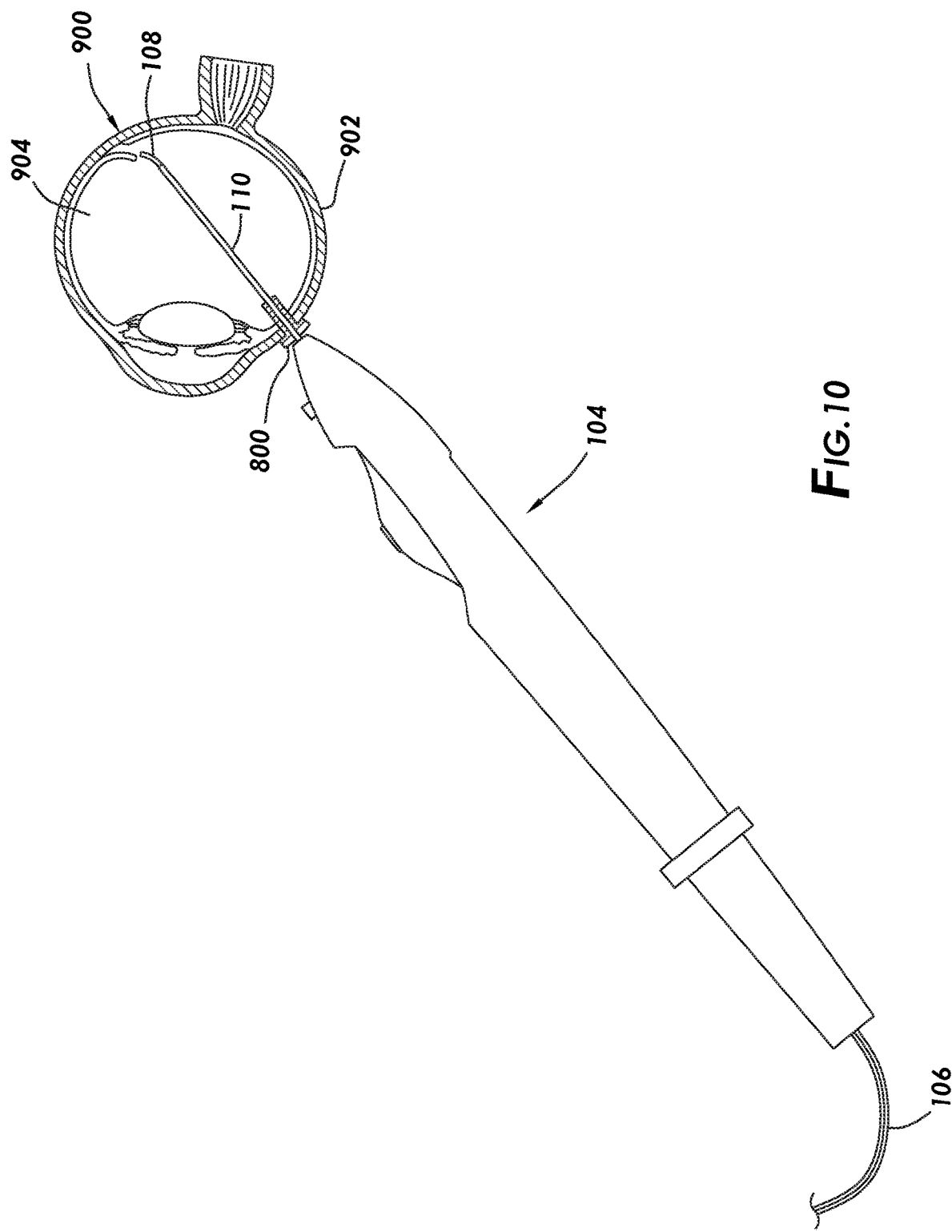
FIG. 10 is a partial cross-sectional view showing the exemplary surgical instrument shown in FIG. 9 advanced toward the retina of an eye with the cannula tip in an extended state according to particular embodiments of the present disclosure.

FIGS. 9 and 10 illustrate partial cross-section views of an eye 900 undergoing a procedure, which may involve the surgical instrument 104 according to an example method of the present disclosure. The surgical instrument 104 may be coupled to a console 102 (e.g., shown on FIG. 1) by way of the supply line 106. During the surgical procedure, the surgeon may insert a working cannula 800 into the eye 900 via an incision through the sclera 902. In FIG. 9, the surgical instrument 104 may be inserted through the working cannula 800 and into a vitreous chamber 904 of the eye 900. As illustrated, the cannula tip 108 may be retracted into the outer tube 242 of the cannula assembly 110 such that cannula tip 108 is obstructed from view on FIG. 9. Because the cannula tip 108 is retracted, particular embodiments may facilitate insertion of the cannula assembly through the hub 802 and into the hollow tube 804 without having to apply undue pressure on the cannula tip 108. FIG. 10 illustrates the cannula tip 108 extended from the cannula assembly 110 after insertion through the working cannula 800 and into the eye 900.

It is believed that the operation and construction of the present disclosure will be apparent from the foregoing description. While the apparatus and methods shown or described above have been characterized as being preferred, various changes and modifications may be made therein without departing from the spirit and scope of the disclosure as defined in the following claims.

What is claimed is:

1. An apparatus for use in an ophthalmic surgical procedure, comprising:
   a housing having a proximal end and a distal end with a valve bay disposed between the proximal end and the distal end;
   a cannula assembly that extends from the distal end of the housing, wherein the cannula assembly comprises:

an outer tube; and an inner tube positioned in the outer tube, wherein the inner tube comprises an elongated portion and a cannula tip attached at a distal end of the elongated portion;

a valve disposed in the valve bay of the housing, wherein the valve comprises a valve tubular coupled to the inner tube for adjusting flow through the inner tube; and an actuator coupled to the valve and the inner tube for moving the cannula tip from an extended position to a retracted position in the outer tube, wherein the valve tubular provides a biasing force to the inner tube in the retracted position to move the inner tube back to the extended position upon release of the actuator.

2. The apparatus of claim 1, wherein a proximal port is formed in the proximal end of the housing for receiving a supply line, and wherein a distal port is formed in the distal end of the housing, the cannula assembly extending through the distal port.

3. The apparatus of claim 1, wherein the housing defines an interior chamber that extends from the proximal end of the housing to the valve bay.

4. The apparatus of claim 1, wherein the valve tubular is flexible and elastic such that the valve tubular stores spring energy to bias the inner tube when deformed by movement of the actuator.

5. The apparatus of claim 1, wherein the valve tubular is formed from a material comprising silicone.

6. The apparatus of claim 1, further comprising a cannula connection mechanism connecting the inner tube and the valve tubular, wherein the actuator extends from the cannula connection mechanism.

7. The apparatus of claim 6, wherein the actuator comprises a button and a connector piece extending from the cannula connection mechanism to connect the button to the cannula connection mechanism.

8. The apparatus of claim 6, wherein the actuator comprises a button having a plurality of ridges for providing a textured surface.

9. The apparatus of claim 1, wherein the actuator is directly coupled to the valve tubular.

10. The apparatus of claim 1, wherein the cannula tip is a soft tip having a durometer value of about 50 A to about 50 D.

11. The apparatus of claim 1, wherein the cannula tip is formed from a material comprising silicone.

12. The apparatus of claim 1, further comprising a sled slidably disposed on the housing, wherein the valve is disposed on the sled.

13. The apparatus of claim 12, wherein the sled comprises a base having a protrusion that supports the valve tubular, wherein the sled further comprises a cannula connection mechanism at a distal end of the sled that couples the inner tube to the valve tubular.

14. A system for ophthalmic surgical procedures, comprising:

a console comprising a housing, a display screen supported by the console, and a processor; a surgical instrument comprising:

a housing having a proximal end and a distal end with a valve bay disposed between the proximal end and the distal end;

a cannula assembly that extends from the distal end of the housing, wherein the cannula assembly comprises:

an outer tube; and an inner tube positioned in the outer tube, wherein the inner tube comprises an elongated portion and a cannula tip attached at a distal end of the elongated portion;

a valve disposed in the valve bay of the housing, wherein the valve comprises a valve tubular coupled to the inner tube for adjusting flow through the inner tube; and an actuator coupled to the valve and the inner tube for moving the cannula tip from an extended position to a retracted position in the outer tube, wherein the valve tubular provides a biasing force to the inner tube in the retracted position to move the inner tube back to the extended position upon release of the actuator; and a supply line configured to couple the surgical instrument to the console.

15. The system of claim 14, wherein the valve tubular is flexible and elastic such that the valve tubular stores spring energy to bias the inner tube when deformed by translation of the actuator.

16. The system of claim 14, further comprising a cannula connection mechanism connecting the inner tube and the valve tubular, wherein the actuator extends from the cannula connection mechanism.

17. The system of claim 14, further comprising a sled slidably disposed on the housing, wherein the valve is disposed on the sled.

18. A method for operating a surgical instrument, the method comprising:

providing the surgical instrument comprising a housing, a cannula assembly that extends from a distal end of the housing, and a valve tubular disposed in a valve bay of the housing, wherein the cannula assembly comprises an outer tube and an inner tube disposed in the outer tube, the inner tube coupled to the valve tubular, wherein the valve tubular is operable for adjusting flow through the inner tube of the cannula assembly;

retracting a cannula tip of the inner tube into the outer tube, wherein the retracting causes the valve tubular to deform and generate spring energy that acts as a biasing force for extending the inner tube back out of the outer tube upon the spring energy being released; and inserting the cannula assembly through a working cannula and into an eye while the cannula tip is retracted into the outer tube.

19. The method of claim 18, further comprising allowing the valve tubular to release at least a portion of the spring energy to move the cannula tip out of the outer tube after the step of inserting the cannula assembly through the working cannula.

* * * * *